United States Patent
Hirata

(10) Patent No.: US 6,521,219 B1
(45) Date of Patent: Feb. 18, 2003

(54) METHOD OF REPAIRING OR RESTORING DAMAGED OR IMPERFECT HAIR

(75) Inventor: Yoshihiro Hirata, Kyoto (JP)

(73) Assignee: Phild Co., Ltd., Kyoto (JP)

( * ) Notice: Subject to any disclaimer, the term of this patent is extended or adjusted under 35 U.S.C. 154(b) by 0 days.

(21) Appl. No.: 09/724,377

(22) Filed: Nov. 27, 2000

Related U.S. Application Data
(60) Provisional application No. 60/230,346, filed on Sep. 6, 2000.

(51) Int. Cl.[7] .............................. A61K 7/06; A61K 7/00; A61K 38/00; A61K 31/195; A01N 37/18
(52) U.S. Cl. .......................... 424/70.1; 424/401; 514/2; 514/21; 514/561; 514/880
(58) Field of Search ................................ 424/401, 70.1; 514/2, 21, 880, 561

(56) References Cited

U.S. PATENT DOCUMENTS

| | | | | |
|---|---|---|---|---|
| 4,220,166 A | * | 9/1980 | Newell | 132/209 |
| 4,855,130 A | * | 8/1989 | Konrad et al. | 424/70.1 |
| 4,906,460 A | * | 3/1990 | Kim et al. | 424/70.14 |
| 6,325,072 B1 | * | 12/2001 | Smetana | 132/228 |

* cited by examiner

Primary Examiner—Jose' G. Dees
Assistant Examiner—Marina Lamm
(74) Attorney, Agent, or Firm—Knobbe, Martens, Olson & Bear LLP

(57) ABSTRACT

Damaged or imperfect hair shafts are treated by: (a) hydrating hair shafts to open flaps of the cuticles layer, (b) applying to the hair shafts amino acids or peptides effective to nourish hair, and (c) compressing the hair shafts under heat by sandwiching the hair shafts between heated plates to cause the amino acids or peptides to penetrate through the cuticle layer and close the openings between the flaps. The penetrated amino acids or peptides nourish the cortex. The hair shafts may be subjected to hair styling treatment.

21 Claims, 1 Drawing Sheet

METHOD OF REPAIRING OR RESTORING DAMAGED OR IMPERFECT HAIR

This application claims the benefit of U.S. Provisional Application No. 60/230,346 filed Sep. 6, 2000.

BACKGROUND OF THE INVENTION

1. Field of the Invention

The present invention relates to a method of repairing or restoring damaged or imperfect hair and a method of nourishing hair. The present invention also relates to a method of styling hair.

2. Description of the Related Art

As shown in FIG. 1, a hair shaft is composed of an outer layer 1 covering the hair shaft, called the cuticle, a protein complex 2 constituting a body of the hair shaft, called the cortex, and a core of the hair shaft 3, called the medulla. The cuticle is composed of the outermost layer having flaps 4 like scales, called the epi-cuticle, the intermediate layer, called the exo-cuticle, and the underlying layer, called the end-cuticle.

When hair contacts chlorinated pool water, is exposed to sunlight, or is improperly brushed, for example, the hair is damaged. That is, the flaps of the cuticle of the hair are disordered or deteriorate, and then the cortex begins deteriorating. When hair is damaged, the hair shafts look dry and non-shiny, and are less resilient than sound hair shafts. Further, many split hair shafts may be observed. Even if hair is not damaged, hair may have received some stimuli causing deterioration, and thus it can be said that no one can have perfect hair.

Numerous types of hair treatment to nourish or repair hair are available on the market. Dominant conventional hair treatments are simple application of a solution, gel, mousse, or mist to hair. These products may be in the form of a shampoo or rinse or in the form of a hair lotion or styling product. However, these products do not provide satisfactory results, because the cuticle layer blocks components in the products from penetrating therethrough. The components, which stay on the surface of the cuticle, cannot repair or restore damaged hair.

SUMMARY OF THE INVENTION

The present inventors have explored hair treatment and discovered deep treatment which can treat the damaged cortex of hair shafts. The present invention includes a method of nourishing hair shafts, each hair shaft comprising a cuticle layer and a cortex enclosed in the cuticle layer, said method comprising the steps of: (a) hydrating hair shafts to open flaps of the cuticles layer, (b) applying to the hair shafts amino acids or peptides effective to nourish hair, and (c) compressing the hair shafts under heat by sandwiching the hair shafts between heated plates to cause the amino acids or peptides to penetrate through the cuticle layer and close the openings between the flaps. The penetrated amino acids or peptides nourish the cortex. In this method, no chemical modification is caused, unlike permanent treatment (although this repairing/restoring method can be used in combination with permanent treatment). In the above, the method can further comprise cooling the treated hair shafts to contract the cuticle layer, wherein the amino acids or peptides are effectively confined in the cortex.

In the above, the hydration step is for rendering the flaps of the cuticle layer lax and opening the flaps. The step can be accomplished by various means including washing, spraying, streaming, etc. The size of a gap between the flaps depends on the degree of hydration, and it is desirable to continue the hydration process until the size of the gap reach an appropriate level (e.g., approximately 10 nm). Hydration depends not only on moisture content but also temperature, and thus in the case of coarse hair (the flaps do not readily open), for example, stream may be effective. The applying step may comprise: after hydrating hair shafts or simultaneously with hydrating step, applying to the hair shafts amino acids or peptides effective to nourish hair. In an embodiment, the treating step may comprise: placing the hair shafts between surfaces having a temperature effective to generate steam; and pressing the hair shafts between the surfaces to generate steam from moisture of the hair shafts and substantially trap the steam around the hair shafts between the surfaces. In an embodiment, the temperature of the surfaces may be in the range of 130° C. to 180° C., preferably 150° C. or higher. Pressurized superheated steam can be produced between the surfaces to generate cracks between the flaps of the cuticle, so that amino acids or peptides can externally be introduced through the cuticle into the cortex.

The amino acids or peptides have a molecular size smaller than the cracks (i.e., openings generated between flaps of the cuticle layer), so that the amino acids or peptides can enter into the cortex through openings generated in the cuticles during the pressurized seam treatment. In an embodiment, the amino acids or peptides have a low molecular weight and have a molecular size of 10 nm or less, preferably 2.5–5.0 nm.

In another embodiment, the hydrating step may comprise: washing the hair shafts; and removing excess water from the hair shafts. Hair has normally a moisture of 10–15%, and upon washing hair, the moisture content increases to 30–35%. The cortex structure includes numerous hydrogen bonds. By increasing the moisture content, hydrogen bonds tend to get loose and break, resulting in swelling of hair and leading to opening the cuticles. In the above, prior to the treating step, the hair shafts preferably contain moisture in an amount of 30% to 90%, preferably 60–80%, of the maximum amount of moisture that the hair shafts can hold.

Further, the cooling step may comprise: rapidly releasing the pressure; and blowing air onto the hair shafts.

In an embodiment, amino acids or peptides may have an average weight molecular weight of 400 to 1,000. Further, amino acids or peptides may have a molecular size of 2 nm to 5 nm. The above amino acids or peptides can easily penetrate through the treated cuticle. The amino acids or peptides should not be limited to but include peptides of hydrolyzed collagen. Conventional nourishing components having small molecular sizes may be used.

In an embodiment, the above method can be applied effectively to damaged or imperfect hair shafts. By conducting the method, the damaged or imperfect hair shafts can be repaired or restored.

The present invention also includes a method of repairing or restoring damaged or imperfect hair shafts, comprising the steps of: determining the condition of hair shafts; and conducting the nourishing method described above in accordance with the determined condition of the hair shafts, wherein the worse the condition of the hair shafts, the more the method is repeated. At hair saloons or beauty parlors, a hairdresser can determine the condition of customers' hair and advise the best treatment.

Further, the present invention includes a method of styling hair, comprising the steps of: conducting the nourishing method described above; and styling the hair. In an embodiment, the styling is permanent treatment. The cortex of the hair shafts treated by the nourishing method described above is resilient, retains water, and comprises sufficient S—S bonds. Further, the cuticle of the hair shafts is aligned in a direction. Thus, the hair shafts can be permed easily and maintain their shape for a long period of time.

For purposes of summarizing the invention and the advantages achieved over the prior art, certain objects and advantages of the invention have been described above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Further aspects, features and advantages of this invention will become apparent from the detailed description of the preferred embodiments which follow.

DETAILED DESCRIPTION OF THE PREFERRED EMBODIMENT

Figure 1:
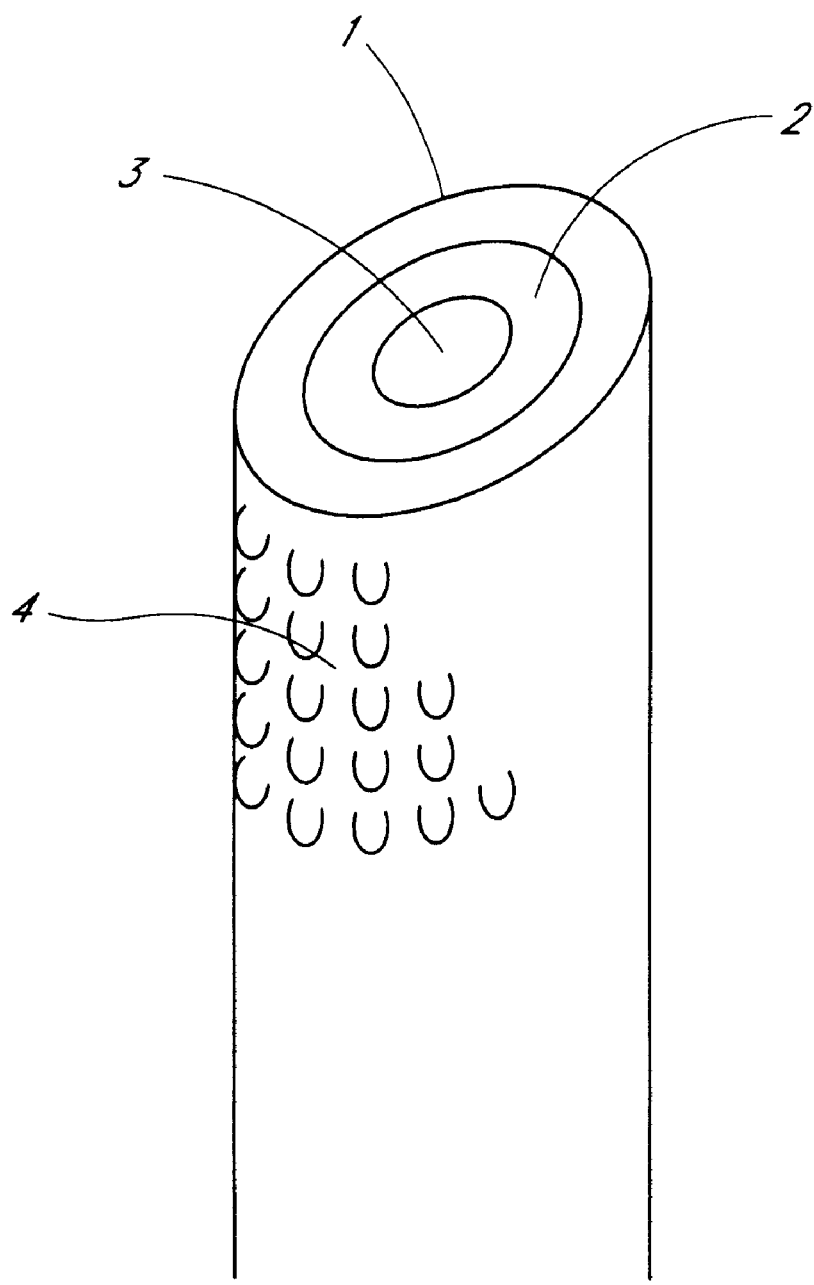
FIG. 1 is a schematic side view showing structures of a hair shaft.

The present invention will be explained in detail below with reference to preferred embodiments. However, the present invention is not limited thereto and includes any modifications which one of ordinary skill in the art can readily practice.

Hair Shafts to be Treated

The present invention is applicable to damaged or imperfect hair. According to various embodiments of the present invention, damaged or imperfect hair can be repaired or restored effectively. However, the term "damaged or imperfect" is not limited to the meaning which laypersons may think of. That is, hair is always exposed and constantly receives physical and chemical impacts caused by brushing and sunlight, for example, and further hair follicles cannot be constantly healthy and hair is likely to have already been damaged when growing from the hair follicles. Thus, no one has perfect hair. In other words, the present invention can be applied to any hair type and is very useful to improve hair condition.

When hair is damaged, some of collagen molecules constituting the cortex have been separated from the main structure of the cortex. The cuticle is damaged, creating cracks, and then through the cracks, collagen molecules come out of the cortex when in contact with moisture. Further, S—S bonds of cysteine are damaged. Collagen molecules are water-soluble and are easily discharged with moisture when the cortex structure has deteriorated. As damages progresses, more collagen molecules tend to be separated from the cortex structure. Collagen molecules are capable of retaining water, and when collagen molecules are lost, the hair is susceptible to drying. The flaps of the cuticle are not reordered, and the cracks created in the cuticle as a result of damage do not close but remain open. Once damage occurs, the damage tends to continue to progress. By applying the present invention as described below, the cortex can be restructured by providing amino acids or peptides through the cuticle layer. If amino acids or peptides are applied simply onto the surface of the cuticle, these components cannot penetrate through the cuticle. Cracks are created as a result of damage because the flaps of the cuticle are disordered and are no longer aligned in a direction. According to embodiments of the present invention, the flaps of the cuticle open and enable amino acids or peptides to penetrate into the cortex, and further, when the flaps close, the flaps are reordered and aligned in a direction, trapping the amino acids or peptides in the cortex wherein the cortex can be repaired or restored. As a result, hair can be smooth, shiny, and resilient. The deep treatment of the present invention is very distinct from conventional surface treatment.

If hair to be treated is perfect hair, the deep treatment of the present invention can nourish the hair. By opening the flaps of the cuticle, nourishing components can be provided into the cortex in the same way as when repairing or restoring hair.

Determination of Damages

The degree of damage present in hair shafts can be determined by observation by the eyes or by a microscope. For example, damaged hair shafts are not smooth or shiny and are less resilient than sound hair shafts. Under a microscope, damage can be observed as disorder of the flap arrangement. Further, damage can be determined based on the moisture content of hair shafts. If the moisture content is less than 9%, the hair shafts are highly likely to be damaged. One of ordinary skill in the art can readily determine the condition of hair shafts, and determine the need for the deep treatment of the present invention.

Steam-Heating Process (Heat-Compressing Process)

In a steam-heating process, when hair shafts are treated by heated steam under pressure which is produced by placing wet or dampened hair shafts between surfaces of a pressing iron set at a temperature of 100° C. to 200° C. (surface temperature), moisture of the hair shafts is trapped between the surfaces of the pressing iron and is instantly heated under pressure, producing pressurized superheated steam. The steam causes the structure of the cuticle, which is the outer layer of hair for protecting hair, to almost instantly loosen its firm structure, producing numerous micro cracks having a width of approximately 10 mn (in other embodiments, the width may range from 2 nm to 50 nm) on the surface of the cuticle layer. The cuticle layer of the heat-processed hair shafts is permeable to amino acids or peptides having a molecular size smaller than the cracks. The cuticle layer is comprised of three layers: The epi-cuticle layer (outermost layer), exo-cuticle layer (intermediate layer), and endo-cuticle layer (underlying layer). The outermost layer is also called the flap layer because numerous flaps are tightly arranged like scales. When wet hair shafts are subjected to the steam-heating process, the epicuticle layer loosens its firm structure, creating micro-cracks (openings) between the flaps. This phenomenon occurs instantly (e.g., one second to fifteen seconds, preferably less than five seconds), when using pressurized superheated steam. If the set temperature of the pressing iron is too low, the above phenomenon does not occur instantly, whereas if the set temperature is too high, the pressing iron may damage hair itself. In an embodiment, the set temperature of the pressing iron may be 130° C. to 180° C., preferably 150° C. to 160° C. Application of the pressing iron may be conducted for a half second to five seconds at a time and can be repeated multiple times. Depending on the type of iron, the application time period can be longer (e.g., 15 seconds to a few minutes). In an embodiment, the application time period (the first pressing) may be less than one second (e.g., approximately 0.5 seconds) at a time and may be repeated at intervals (e.g., approximately 0.5 seconds) until the moisture content is reduced to approximately 20–30% (the moisture content of normal hair shafts is 10–15%). Thereafter, the application time period (the second pressing) may be prolonged to 2–3 seconds at a time and may be repeated at intervals until the treatment is complete. The first pressing is mainly for exciting water molecules, cleaving hydrogen bonds, further opening the cuticles, and causing the amino acids or peptides to penetrate into the cortex. The second pressing is mainly for orienting the cuticles and closing the cuticles. The above combination can be very effective in the steam-heating treatment. In the above, during each interval, the hair is cooled and dried, thereby gradually loosing moisture. Thus, a separate cooling step need not be conducted. In this case, the steam-heating process includes a cooling process.

The amount of hair shafts to be treated at a time is such that each hair shaft is effectively subjected to the steam-heating treatment using a pressing iron. The amount of hair shafts depends on the type of pressing iron, the temperature, and the quality of hair. In an embodiment, upon combing hair, a bundle of hair having a width of 1.5–2.0 cm is pressed between plates of a pressing iron, i.e., a thickness of the bundle may be approximately 1 mm when pressed between the plates. If too much hair is subjected to pressing at a time, the temperature of hair shafts cannot increase sufficiently and moisture may not diffuse well.

Further, the moisture content of hair is important to produce pressurized superheated steam as described below. The second layer of the cuticle (exo-cuticle) has a porous structure as compared with the outermost layer of the cuticle (epi-cuticle). Thus, when the epi-cuticle's firm structure is loosened, amino acids or peptides having a small molecular size, which are externally provided, can enter into the cortex of hair (protein complex formed around the core called medulla). The small gap between the surfaces of the pressing iron is under pressure due to the presence of heated steam. Externally provided amino acids or peptides can readily penetrate into the cortex of hair.

Further, by the steam-heating process, the cuticle of the hair shaft is subjected to reorder or reconstruction and is aligned in the natural or original direction.

The pressing iron can be of any type which is capable of generating steam and heating it to 100° C. to 200° C. (close to the surface temperature) and pressing hair shafts between its surfaces, so that moisture can be trapped between the surfaces, heated, and vaporized instantly, generating pressurized superheated steam in the gap between the surfaces. In an embodiment, the pressuring iron may be a flat iron having two flat plates (having a width of approximately 6 cm, for example) to sandwich hair shafts and trap steam therebetween. One or both of the plates can be heated. For example, a flat iron traded under PHITEN REPAIR IRON™ (Model EH61-05) by PHI-TEN U.S.A. (California) can be used. The surfaces need not be flat and can be curved as long as hair shafts can be in surface contact with the surfaces. The surface contact is effective to generate pressurized heated steam. In an embodiment, a roller type iron can be used which accommodates hair shafts between heated rollers. In the case of a flat iron having two plates, in order to trap steam under pressure, the width of the plates may be in the range of 4 cm to 8 cm, and a bundle of hair shafts (approximately 10 to 100 shafts) may be treated at a time. If too many shafts are placed on the plate or if the width of the plate is too small, steam may not be trapped around the hair shafts and thus may be neither pressurized nor superheated.

Hydration Process Prior to Heat-Compressing Process

Prior to the steam-heating process (heat-compressing process), the hair shafts are moisturized. The moisture content of hair shafts to be treated may be approximately 30% to 90%, preferably 60% to 80%, with respect to the moisture content immediately after hair is washed and excess water is removed from the hair (referred to as the moisture content of washed hair or the maximum capacity of holding moisture). Removal of excess water can be conducted by wiping hair with a towel, for example. In an embodiment, the moisture content of hair shafts may be approximately 70% with respect to the moisture content of washed hair. When hair is fully hydrated, the moisture content of the cortex is approximately 30% to 35% (originally 10% to 15%). To fully hydrate hair, it may take 2 minutes to 10 minutes after hair is in contact with water. If the moisture content of hair is too low, insufficient steam is produced when the hair is subjected to the heat-compressing process, and hair may be damaged by heat. If the moisture content is too high, vaporization of moisture does not occur instantly and insufficient pressure and heat may be applied to hair, and the skin may get burned when hot water drops fall thereon. The flaps of the cuticle layer of hydrated hair shafts open so that small-size molecules can penetrate through the cuticle layer. If the degree of openings between flaps is insufficient for the above purpose, the hair shafts can be subjected to, for example, an additional steaming process as described later.

By washing hair, the hair can be moisturized and swollen. After washing hair, the hair is dried until the moisture content is reduced to a desired level if necessary. Any other means equivalent to washing can be employed in the present invention. For example, simply soaking or moisturizing hair with water may be sufficient, or simply spraying water onto hair prior to the heat-compressing process may be sufficient, as long as the moisture content of the hair reaches a desired level as described above. If the moisture of the hair shafts is not in the above range prior to the heat-compressing process, the moisture can be adjusted by any type of hair treatment. Washing hair prior to the heat-compressing process (but need not be immediately before the heat-compressing process) may enhance the effect of the heat-compressing process by removing oil and dirt which may interfere with the treatment.

Amino Acids and Peptides

In the present invention, in addition to moisturization of hair, amino acids or peptides for repair or restoration of damaged or imperfect hair are provided to hair prior to the heat-compressing process. Amino acids or peptides can be introduced simultaneously with water when moisturizing hair, although they can be added separately from water. In an embodiment, an aqueous solution containing amino acids or peptides may be used. Hair shafts are moisturized by contacting an aqueous solution containing amino acids or peptides having a molecular size smaller than the cracks created in the cuticle layer by the heat-compressing process. In an embodiment, the size of amino acids or peptides may be in the range of approximately 1 nm to 10 nm (in an embodiment, 2.5 nm to 5 nm). For example, a hydrolyzed collagen has a molecular size of approximately 3 nm.

When cracks (openings) are produced in the cuticle layer, amino acids or peptide molecules having a size smaller than the cracks can penetrate through the cuticle layer into the cortex. Since the intermediate and underlying layers of the cuticle (exo- and endo-cuticle layers) are porous as compared with the outermost layer of the cuticle (epi-cuticle), when the cracks are created between flaps of the epi-cuticle layer, amino acids or peptides can penetrate through the cuticle layer of hair shafts and reach the cortex which is a protein complex formed around the medulla (the core of the hair structure).

Amino acids or peptides usable in the present invention can be any amino acids or peptides which are capable of nourishing, repairing, or restoring damaged or imperfect hair shafts by penetrating into the cortex through the cracks created between flaps of the cuticle. They include water-soluble proteins having a small molecular weight such as 100 to 10,000 (in an embodiment, 400 to 1,000), which include hydrolyzed collagen (a molecular size of 3 nm) including, but not limited to, ampd-isostearoyl hydrolyzed collagen and hydroxypropyltrimonium hydrolyzed collagen. Other amino acids and peptides usable in the present invention include hydroxypropyltrimonium hydrolyzed keratin, N-[2-hydroxy-3-(cocoalkyldimethylammonia)propyl] hydrolyzed keratin chloride, hydrolyzed animal protein, trimethylglycine, glycine, L-alanine, L-proline, L-serine, L-threonine, L-arginine, L-lysine, L-glutamic acid, N-[2-hydroxy-3-(trimethylammonio)propyl]hydrolyzed collagen chloride, and a mixture of any of the foregoing. Further, additionally, 1,3-butyleneglycol, sodium d1-pyrrolidonecarboxylate, parahydroxybenzoate ester, 2-phenoxyethanol, or a mixture of any of the foregoing can be used. The cortex of damaged or imperfect hair has an insufficient collagen content, and the amino acids or peptides can compensate for the insufficiency and restore the cortex structure. The amino acids or peptides are capable of retaining water, and thus hair itself can become smooth, shiny, and resilient. Conventional treatments could not provide amino acids or peptides into the cortex but simply applied amino acids or peptides on the surface of the cuticle, and thus conventional treatments could not repair or restore damaged or imperfect hair.

An aqueous solution may contain amino acids or peptides at a concentration of 4–10% by weight, for example. The aqueous solution may contain other components such as humectants (such as 1,3-butylene glycol, sodium hyaluronate, hydrolyzed elastin, plant extract, seaweed extract, hydrolyzed silk powder, and L-glutamic acid), surface active agents, pH adjusting agents, vitamins, and preservatives. The humectants may be contained in an amount of 3–6% by weight. Additionally, methylpolysiloxane can be included for smooth combing.

The amount of an aqueous solution to be used is 20–50 cc for short hair. If the solution is sprayed onto hair while combing hair, 2–5 cc may be sprayed at a time. The aqueous solution can be applied to hair at two or three times if rinsing is conducted to repeat the moisturizing step.

In an embodiment, two types of aqueous solution are used in combination: One includes amino acids, and the other includes hydrolyzed collagen. If the two types are used in combination, the stream-heating treatment can be performed effectively. Further, for fine hair, hydrolyzed keratin can be included in an aqueous solution.

For example, for coarse hair, the following two types of solution may be used:
(a) Protein Solution A: 4–6% of L-glutamic acid, 1–2% of methylpolysiloxane, 4–6% of hydrolyzed collagen, and 2–4% of hydrolyzed keratin.
(b) Protein Solution B: 8–10% of hydrolyzed collagen, 2–4% of hydrolyzed keratin, 12% of hydrolyzed elastin.
For fine hair, the following two types of solution may be used:
(c) Protein Solution C: 4–6% of L-glutamic acid, 1–2% of methylpolysiloxane, 4–6% of hydrolyzed collagen.
(d) Protein Solution D: 4–8% of hydrolyzed keratin, 8–10% of hydrolyzed collagen. In the above, Protein Solutions B and D may contain 2–6% of humectants such as those listed above.

In the above, the solution can contain peptides having larger molecular sizes than the aforesaid small-molecular size peptides, in a concentration of 2–10%, so that not only the inside but also the outside of the hair shafts can be treated with peptides.

Cooling Process

Upon the heat-compressing process, a cooling process is initiated to effectively cool the hair shafts and rapidly close the cracks of the flaps, so that the amino acids or peptides which have entered into the cortex can be maintained in the cortex. However, if a pressing iron is used, the cooling process is conducted during each interval between intermittent pressing operations. In this case, the cooling process is conducted during the heat-compressing process. In an embodiment, the cooling process can be conducted simply by releasing the pressing iron quickly, so that pressurized superheated steam can vaporize quickly due to a sudden reduction of the pressure. The temperature is also reduced rapidly due to radiation of heat of vaporization. When releasing the pressing iron, air-blowing the hair can be conducted to accelerate vaporization of the steam. When the flaps cool, the cracks close and trap the amino acids or peptides inside in an embodiment. The temperature may go down to a body temperature or room temperature in 2 seconds to several minutes in an embodiment. The amino acids or peptides can remain in the cortex impregnated therewith and can repair or restore a damaged cortex from which collagen has been discharged. After the flaps of the cuticle close, the cuticle structure regains its strength and the amino acids or peptides are not discharged easily.

Additional Processes

After moistening hair prior to the heat-compressing process, the hair can be subjected to steaming treatment to fully hydrate the hair. The cuticle is highly hydrated, thereby accelerating the subsequent heat-compressing treatment to open the flaps of the cuticle and provide amino acids or peptides into the cortex. For example, this process can be conducted by covering the hair with a hot wet towel or a steamer for a few minutes to 30 minutes, preferably 10–15 minutes. The moisture content of the hair can remain at a desired level (30% to 90% of the moisture content of washed hair).

The steaming process can be conducted after the application of the amino acids or peptides but before the heat-compressing process.

After the steaming process, cooling and drying may be conducted prior to the heat-compressing process. The cooling process is for uniformly settling the amino acids or peptides.

Prior to the heat-compressing process, hair can be washed slightly to remove excess amino acids or peptides.

After the heat-compressing process, the hair can be washed to remove residues from the surface of the hair shafts.

Effects of the Processes and Hair Styling

According to various embodiments of the present invention, damaged or imperfect hair can be repaired or restored effectively. Further, surprisingly, when the treated hair is styled, e.g., waved or straightened, the styled hair can last significantly longer than does the conventionally treated hair. This may be because amino acids or peptides can penetrate into the cortex and prevent cysteine from being discharged and can further reestablish S—S bonds which contributes to maintaining the style of hair. In the conventional treatments, the above effects cannot occur because no components can penetrate through the cuticle into the cortex. The surface of the cuticle is exposed and thus no treatment components can stay on or affect the cortex. According to an embodiment of the present invention, even split hair shafts can be waved or straightened because the damaged cortex of the split hair shafts can be repaired or restored effectively. Conventionally, split hair shafts cannot be waved or straightened because the cortex of split hair shafts is damaged and cannot sufficiently be treated chemically. Conventional surface treatment of hair is not effective for split hair shafts. In contrast, deep treatment of the present invention is highly effective not only to improve the appearance of hair but also to enhance the effects of permanent treatment, as well as to enable treatment of damaged hair such as split hair shafts.

Hair treated by the present invention is smooth, shiny, and resilient, and possesses characteristics of undamaged natural hair. Since hair is always exposed and constantly receives physical and chemical impacts caused by brushing and sunlight, for example, and further hair follicles cannot be constantly healthy and hair is likely to have already been damaged when growing from the hair follicles, no one has perfect hair. The present invention can be applied to any hair type and is very useful to improve hair quality.

EXAMPLE

Straight black hair of an Asian, which was slightly damaged by sunlight at a beach, looked dry, and microscope observation showed that its cuticle was slightly disordered. The moisture content was 9%. The hair was treated as follows:

(1) The hair was washed once with a conventional shampoo in a conventional manner. If hair is already clean, and no styling product is applied, hair is wetted with water.

(2) After the hair was washed, the hair was wiped with a towel to remove excess water from the hair. The hair was damp but no water dripped. 30 cc of a 5% L-glutamic acid solution (a 5-times diluted solution of SE PLAIRE TREATMENT FOR THICK HAIR™ from PHI-TEN U.S.A. (California)) were applied using a spray to the hair, and the hair was combed well to evenly spread the solution throughout the hair. In the above, for thin hair, SE PLAIRE TREATMENT FOR THIN HAIR™ from PHI-TEN U.S.A. (California) can alternatively be used.

(3) After applying the solution, 30 cc of a 5% hydrolyzed collagen solution (PPT PRO™ from PHI-TEN U.S.A. (California)) were applied using a spray onto the hair. The collagen solution was thoroughly and gently applied to damaged portions of the hair. In the above, for thin hair, HAIR ESSENCE PRO™ from PHI-TEN U.S.A. (California) can alternatively be used.

(4) The hair was then subjected to steaming. A steamer was placed over the head, and the hair was steamed for 15 minutes. If a steamer is not available, a wet warm towel can be used, and a hair cap can also be used.

(5) The hair was then cooled by letting the hair cool for 5 minutes after removing the steamer.

(6) After the cooling, the hair was dried by blowing air with a drier until large bundles of hair shafts became loose and separated but the hair was still damp. The moisture content of the hair was reduced to approximately 40% of the moisture content of the washed hair. The hair was let stand for 5 minutes.

(7) After the drying, the hair was gently and slightly rinsed with warm water to remove excess solution.

(8) 20 cc of the L-glutamic acid solution was then applied to the hair, and the hair was gently and slightly rinsed with water.

(9) The hair was then dried again by blowing air with a drier until large bundles of hair shafts became loose and separated but the hair was still damp. The moisture content of the hair was reduced to approximately 20–40% of the moisture content of the washed hair.

(10) After the drying, the hair was subjected to patate press using a flat iron (PHITEN REPAIR IRON™ (Model EH61-05) from PHI-TEN U.S.A. (California)). The temperature setting was 150° C.–180° C. Upon combing the hair, a bundle of hair having a width of 1.5–2.0 cm was pressed between the plates of the flat iron. The application time period (the first pressing) was approximately 0.5 seconds at a time and was repeated at intervals (approximately 0.5 seconds) until the moisture content was reduced to approximately 20–30%. Thereafter, the application time period (the second pressing) was prolonged to 2–3 seconds at a time and was repeated at intervals until the treatment was complete. If hair ends are too dry, water is applied before pressing.

The hair shafts were observed with a microscope. It showed that the flaps of the cuticle were ordered and aligned in a direction. The hair shafts were much smoother, shinier, and more resilient than the untreated hair.

The treated hair was washed to remove residues from the surface of the hair shafts. Sample hair shafts were collected from the hair and placed in a desiccator cabinet for a few hours. The moisture content of the sample hair shafts was then measured, showing 14%. The cortex of the treated hair contained more moisture than that of the untreated hair.

The sample of the treated hair was subjected to permanent treatment to make the hair shafts wavy. As a control, a sample of the original hair, which had previously been collected, was treated in the same way as the above except for the heat-compressing process (the moisture content was 10%). The permanent treatment was conducted on the samples on an experimental scale based on conventional permanent treatment. Durability of the permed hair shafts was tested by washing them with soap and water multiple times. As a result, it was confirmed that the treated hair shafts had much better durability and maintained its wavy shape, whereas the control sample did not maintain its wavy shape after the second wash. This shows that the cortex of the treated hair was significantly repaired.

The same effects were observed in various types of hair.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A method of nourishing hair shafts, each hair shaft comprising a cuticle layer and a cortex enclosed in the cuticle layer, said method comprising the steps of:

hydrating hair shafts to open flaps of the cuticle layer;

applying to the hair shafts amino acids and/or peptides for hair nourishment having a molecular size smaller than the gaps between the flaps, wherein said amino acids and/or peptides are present in the openings between the flaps; and then compressing the hair shafts under heat by sandwiching the hair shafts between plates heated to above a boiling point to generate steam between the plates and simultaneously to press the flaps of the cuticle layer, whereby the amino acids and/or peptides penetrate through the cuticle layer and are confined inside the hair shafts.

2. The method according to claim 1, further comprising cooling the treated hair shafts to contract the cuticle layer.

3. The method according to claim 1, further comprising, between the applying step and the heat-compressing step, steaming the hair shafts to further open the flaps of the cuticle layers.

4. The method according to claim 1, wherein in the applying step, the amino acids and the peptides are separately applied.

5. The method according to claim 1, wherein the heat-compressing step comprises:
   placing the hair shafts between the heated plates, wherein said plates have flat surfaces; and
   intermittently pressing the hair shafts between the surfaces to generate steam from moisture of the hair shafts and substantially trap the steam around the hair shafts between the surfaces.

6. The method according to claim 1, wherein the temperature of the plates is in the range of 130° C. to 180° C.

7. The method according to claim 2, wherein the cooling step comprises:
   rapidly releasing the pressure; and
   blowing air onto the hair shafts.

8. The method according to claim 1, wherein, prior to the heat-compressing step, the hair shafts contain moisture in an amount of 30% to 90% of the maximum amount of moisture that the hair shafts can hold.

9. The method according to claim 1, wherein the peptides have an average weight molecular weight is 400 to 1,000.

10. The method according to claim 1, wherein the amino acids have a molecular size of 2 nm to 6 nm.

11. The method according to claim 1, wherein the amino acids or peptides are a product of hydrolyzed collagen.

12. The method according to claim 1, wherein the amino acids and/or peptides are selected from the group consisting of N-[2-hydroxy-3-(cocoalkyldimethylammonia)propyl] hydrolyzed keratin chloride, hydrolyzed animal protein, trimethylglycine, glycine, L-alanine, L-proline, L-serine, L-threonine, L-arginine, L-lysine, L-glutamic acid, N-[2-hydroxy-3-(trimethylammonio)propyl]hydrolyzed collagen chloride, and a mixture of any of the foregoing.

13. The method according to claim 1, wherein the hair shafts to be treated are damaged or imperfect hair shafts.

14. A method of repairing or restoring damaged or imperfect hair shafts, comprising the steps of:
   determining the condition of hair shafts; and
   conducting a method of claim 1 in accordance with the determined condition of the hair shafts, wherein the worse the condition of the hair shafts, the more the method is repeated.

15. A method of styling hair, comprising the steps of:
   conducting a method of claim 1; and
   styling the hair.

16. The method according to claim 15, wherein the styling is permanent treatment.

17. A method of nourishing hair shafts, each hair shaft comprising a cuticle layer and a cortex enclosed in the cuticle layer, said method comprising the steps of:
   hydrating hair shafts to a moisture content of approximately 30–40%;
   applying to the hair shafts amino acids and/or peptides effective to nourish hair in an amount sufficient to uniformly cover the hair shafts, said amino acids and/or peptides having a molecular size of no more than approximately 10 nm;
   then placing the hair shafts between surfaces having a temperature of 130° C. to 180° C. effective to generate steam;
   pressing the hair shafts between the surfaces to generate steam from moisture of the hair shafts and substantially trap the steam around the hair shafts between the surfaces without damaging the cuticle layer, wherein the cuticle layer is rendered lax, through which the amino acids and/or peptides penetrate into the cortex, and flaps of the cuticle layer are oriented in a direction;
   rapidly releasing the pressure to cool the pressed hair shafts to contract the cuticle layer; and
   repeating the pressing step and the cooling step until the flaps of the cuticle layer are closed, wherein the amino acids and/or peptides nourish the cortex.

18. The method according to claim 17, further comprising, between the applying step and the pressing step, steaming the hair shafts; and cooling the hair shafts.

19. The method according to claim 17, wherein in the applying step, the amino acids and the peptides are separately applied.

20. The method according to claim 17, wherein the peptides have an average weight molecular weight is 400 to 1,000.

21. The method according to claim 17, wherein the amino acids and/or peptides are a product of hydrolyzed collagen.

* * * * *